United States Patent
Raley et al.

[11] Patent Number: 5,827,182
[45] Date of Patent: Oct. 27, 1998

[54] MULTIPLE LED SETS IN OXIMETRY SENSORS

[75] Inventors: Dena Raley, Louisville; Robert Nichols, Thornton, both of Colo.

[73] Assignee: Ohmeda Inc., Liberty Corner, N.J.

[21] Appl. No.: 829,258

[22] Filed: Mar. 31, 1997

[51] Int. Cl.[6] .................................................. A61B 5/00
[52] U.S. Cl. ........................................................... 600/323
[58] Field of Search .................................. 600/310, 322, 600/323, 331; 356/41

[56] References Cited

U.S. PATENT DOCUMENTS

| Re. 33,360 | 10/1990 | Reynolds et al. | 128/675 |
|---|---|---|---|
| 3,720,201 | 3/1973 | Ramsey, III | 128/2.05 D |
| 3,785,367 | 1/1974 | Fortin et al. | 128/2 F |
| 3,890,842 | 6/1975 | Ramsey, III | 73/420 |
| 3,890,962 | 6/1975 | Ramsey, III | 128/2.05 D |
| 3,942,514 | 3/1976 | Ogle | 128/2 F |
| 4,036,216 | 7/1977 | Ramsey, III | 128/2.05 D |
| 4,135,509 | 1/1979 | Shannon | 128/2.05 D |
| 4,557,269 | 12/1985 | Renolds et al. | 128/675 |
| 5,058,588 | 10/1991 | Kaestle | 600/323 |
| 5,086,777 | 2/1992 | Hishii | 128/675 |
| 5,314,410 | 5/1994 | Marks | 604/168 |

Primary Examiner—Max Hindenburg
Assistant Examiner—Eric F. Winakur
Attorney, Agent, or Firm—Roger M. Rathbun

[57] ABSTRACT

The present invention is directed to an oximeter sensor that may be employed with a variety of oximeter processing and display units. The oximeter sensor includes a plurality of radiation emitting devices that are capable of providing a spectral content that is useful in the correlation of a number of different oximeter processing and display units. The oximeter sensor further includes a plurality of resistors, with each resistor being connected to a different oximeter processing and display unit to permit the particular oximeter processing and display unit to select an appropriate correlation curve.

23 Claims, 6 Drawing Sheets

MULTIPLE LED SETS IN OXIMETRY SENSORS

FIELD OF THE INVENTION

The present invention relates generally to oximetry sensors and specifically to oximetry sensors employable with a variety of oximeter processing and display units.

BACKGROUND OF THE INVENTION

Oximetry is commonly used by health care providers to non-invasively identify potential problems with a patient's respiratory and circulatory systems. The color of blood, and the corresponding amounts of red and infrared radiation absorbed by the blood, is a function of the oxygen saturation of the heme in the blood's hemoglobin, (i.e., the relative amounts of oxygenated and deoxygenated hemoglobin in the blood). Heme that is saturated with oxygen (oxygenated hemoglobin) appears bright red as the oxygen saturated heme is highly permeable to red light. In contrast, heme that is deoxygenated (deoxygenated hemoglobin) appears dark and bluish as the deoxygenated heme is less permeable to red light. Typically, an oximeter measures the oxygen saturation of arterial blood by irradiating the blood with red and infrared radiation and determining the respective amounts of red and infrared radiation that are absorbed by the oxygenated and deoxygenated hemoglobin in the blood.

The oximeter typically includes an oximeter sensor for measuring the unabsorbed radiation and an oximeter processing and display unit for converting the unabsorbed radiation measurement into blood oxygen saturation. The sensor typically includes two LED's for irradiating the blood and a radiation detector for receiving the unabsorbed radiation.

Oximeter sensors typically employ separate red and infrared LEDs to provide the desired radiation spectrum for determination of the oxygen saturation of the blood and a correlating curve to permit correlation between (a) the oxygen saturation level of the blood and (b) the ratio of radiation absorption for the red LED to that for the infrared LED. A typical correlation curve is illustrated in FIG. 1. Generally, the spectral content of the red LED is centered around 660 nm in the red region and the spectral content of the infrared LED spectral emission is centered between 800 and 1,000 nm in the near-infrared or infrared region.

The central wavelengths corresponding to the spectral contents of the red and infrared LEDs can have a wide degree of variability which can lead to erroneous oxygen saturation measurements. Any shift in the central wavelength of the LED can cause the oximeter to work with an improper correlation curve and therefore yield an erroneous oxygen saturation measurement. Each correlation curve is specific for a specific central wavelength pairing of the spectral contents of the red and infrared LED's.

To account for the normal variations in the central wavelengths corresponding to the spectral contents of red and infrared LEDs, the oximeter memory may contain a number of correlation curves (or correlation equations) (hereinafter collectively referred to as "correlation curves"), each identified by a corresponding resistor, for instance. By way of example, if a manufacturer has 10 possible central wavelengths corresponding to each of the spectral contents of the red LEDs and three for each of the spectral contents of the infrared LEDs, the oximeter would contain 30 correlation curves, or one correlation curve for each possible pairing of the red and infrared LEDs. To permit the correct correlation curve to be selected, each sensor typically has a resistor that the oximeter processing and display unit checks when the sensor is plugged into the unit. Each different resistance value is indexed to a specific correlation curve.

One manufacturer's sensor is typically not interchangeable with another manufacturer's sensor. Different oximeter manufacturers generally use different red and infrared LEDs producing distinctly different spectral contents and, therefore, use different correlation curves.

Because health care providers may typically have oximeters produced by different manufacturers, health care providers must not only purchase and inventory multiple lines of sensors but also take precautions to issue to health care personnel the corresponding sensor for each type of oximeter being used by such personnel. Such precautions include marking of the sensors and training of health care personnel. The purchase and inventory of multiple lines of sensors for a number of different oximeters and the implementation of the precautions increase health care costs. The sensors may not be compatible with the various types of oximeter processing and display units used by the various departments of the health care provider. Accordingly, the sensors can accompany a patient as he is moved from one health care department to another health care department only if a common type of unit is used by the departments.

SUMMARY OF THE INVENTION

It is an objective of the present invention to provide an oximetry sensor that is interchangeable with a variety of oximeter processing and display units. More specifically, the objective is to provide an oximetry sensor that is interchangeable with oximeter processing and display units produced by different manufacturers.

The present invention addresses these and other objectives by providing a sensor adaptable to a variety of oximeter processing and display units. The sensor includes: (a) measuring means for providing a signal related to oxygen level in the patient's blood (the signal being a function of an unabsorbed portion of radiation passed by the blood) and (b) connecting means for connecting the measuring means with an oximeter processing and display unit. The measuring means includes (i) emitter means for irradiating the blood and (ii) detecting means for detecting the unabsorbed portion of radiation passed by blood. The emitter means includes a plurality of emitters for providing radiation, each of the emitters having a spectral content. Typically, the plurality of emitters is three or more emitters. In a first mode, a first set of the plurality of emitters is activated to generate a first spectral content set (the first spectral content set including the spectral contents of the first set of emitters) and in a second mode, a second set of the emitters is activated to generate a second spectral content set (the second spectral content set including the spectral contents of the second set of emitters) The first and second cumulative spectral content sets are different (i.e., have one or more emitter spectral contents and/or emitters that are not in common). As will be appreciated, each of the spectral content sets includes the spectral contents of each of the emitters sequentially energized to produce the particular spectral content set.

The applicability of the sensor for use with a variety of oximeter processing and display units stems from the sensor's ability to produce the different spectral content sets. By way of example, first and second emitters can be selectively energized to produce the first spectral content set that corresponds to a first correlation curve in a first oximeter processing and display unit, and first and third radiation emitting devices can be selectively energized to produce the second spectral content set that corresponds to a second correlation curve in a second oximeter processing and display unit. The first correlation curve differs from the second correlation curve. The sensor of the present invention therefore can replace the multiple lines of sensors currently purchased and inventoried by health care providers. As a result, the sensor of the present invention significantly reduces health care costs because only one sensor type would be stocked.

To provide adaptability of the measuring means to different oximeter processing and display units, the connecting means can include first and second interconnect cables respectively having first and second oximeter plugs, with the first oximeter plug having a pin configuration suitable for the first oximeter processing and display unit and the second oximeter plug having a configuration suitable for the second oximeter processing and display unit. Thus, the first and second oximeter plugs have different pin configurations. Each of the interconnect cables can respectively include first and second sensor plugs that are interchangeable with connectors on the measuring means. Thus, the first and second sensor plugs, unlike the first and second oximeter plugs, have the same pin configuration in that the plugs are physically arranged the same even though the pins are not electrically connected in the same manner.

In one embodiment, a first emitter provides infrared radiation and second and third emitters red radiation. "Infrared radiation" refers to radiation having a wavelength range from about 930 to about 950 nm. "Red radiation" refers to radiation having a wavelength range from about 640 to about 680 nm.

In this embodiment, first, second, and third spectral contents are significantly different from one another. In other words, the central wavelengths characterizing each of the first, second and third spectral contents are different. In another embodiment, first, second and third emitters are connected to separate connecting points on the connector or are connected to the same connecting points but are oppositely polarized to permit the devices to be activated independently from one another. Thus, when the first emitter is activated by the oximeter processing and display unit, the second and third emitters are not activated by the oximeter processing and display unit. Conversely, when the second emitter is activated by the oximeter processing and display unit, the first and third emitters are not activated by the oximeter processing and display unit.

In a further embodiment of the present invention, the sensor includes a first and second identification means for identifying the above-noted first and second correlation curves. The oximeter processing and display unit selects one of the first and second correlation curves based on one of the first and second identification means. Thus, the first oximeter processing and display unit selects the first correlation curve based on the first identification means, and the second oximeter processing and display unit selects the second correlation curve based on the second identification means. By way of example, the first and second identification means can provide different values for selected electrical parameters (e.g., resistance, current, or voltage) to enable curve selection. As will be appreciated, some oximeter processing and display units employ only one correlation curve and therefore may employ no identification means.

DETAILED DESCRIPTION

Figure 1:
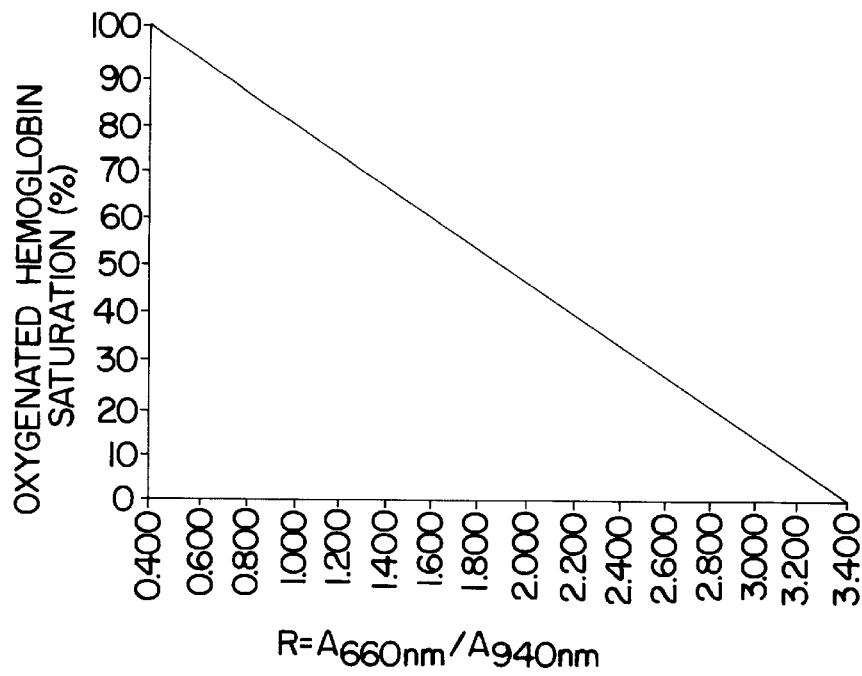
FIG. 1 is a plot of (i) oxygenated hemoglobin saturation against (ii) the ratio "R" of absorbance of a spectral content having a central wavelength of 660 nm ($A_{660}$) to absorbance of a spectral content having a central wavelength of 940 nm ($A_{940}$)

As shown in FIGS. 2–8, the sensor assemblies 2a,b each includes a measuring means 10a,b and an interconnect cable 4a,b. The measuring means 10a,b each includes (i) a sensor housing 14 containing (a) a detector 18, (b) each first, second and third emitters 22, 26, and 30, (c) identification means 50, 54, and (d) a leadframe 60; (ii) connector 6a,b; and (iii) an interconnect cable 4a,b. The connector 6a,b connects to a sensor plug 8a,b on one end of the interconnect cable 4a,b, and an oximeter plug 12a,b on the other end of the interconnect cable 4a,b connects to the corresponding oximeter processing and display unit 16a,b. The arm 21 of the measuring means is bent about the axis A—A to conform to the shape of a body part, such as the tip of a finger, to place the detector 18 in an opposing relationship to the emitters 22, 26, and 30. The adhesive on areas 14 and 23a,b,c is used to hold the measuring means in position on the body part. Two or more of the emitters then sequentially illuminate the body part, with the unabsorbed radiation from each illumination being received by the detector 18. The detector 18 generates an output signal in response to the unabsorbed radiation received by the detector, with the output signals being employable to determine the oxygen saturation of the blood.

The sensor housing 14 and 23a,b,c in the measuring means 10 is composed of a material that is substantially opaque to light with transparent windows 42a,b located over the detector and radiation emitting devices to pass radiation.

The detector 18 is preferably a photodiode or other suitable device for producing an electrical signal in response to the incidence of radiation on the detector surface. As will be appreciated, the current output of a photodiode is directly related to the amount of radiation contacting the detector surface. Thus, in a typical application, the photodiode will produce a time-varying signal in response to the contact of time-varying amounts of radiation upon the detector surface.

The emitters are preferably LEDs which are broad band radiation sources providing substantially different spectral contents (i.e., the spectral contents are characterized by different central wavelengths). The first emitter 26 typically provides infrared radiation while the second and third emitters 22 and 30 provide red radiation.

The spectral contents provided by the emitters 22, 26 and 30 can be grouped to provide a spectral content set that corresponds to the different correlation curves used by different oximeter manufacturers. This permits the sensor assembly 10 to be used with oximeter processing and display units manufactured by the different oximeter manufacturers. By way of example, in a first mode at least two of the first, second and third emitters 22, 26 and 30 are sequentially activated to provide a first spectral content set corresponding to a first correlation curve used by a first set of oximeter processing and display units, and in a second mode at least two of the first, second and third emitters 22, 26 and 30 are sequentially activated to provide a second spectral content set corresponding to a second correlation curve used by a second set of oximeter processing and display units. The first cumulative spectral content is different from the second cumulative spectral content; the first correlation curve is different from the second correlation curve; and the first set of oximeter processing and display units is different from the second set of oximeter processing and display units. As will be appreciated, the set of emitters sequentially activated in the first mode is different from the set of emitters sequentially activated in the second mode.

A common infrared emitter is typically used with different sets of red emitters to provide the desired spectral content sets. As will be appreciated, it is nonetheless possible to use a common red emitter with two different infrared emitters.

The red and infrared emitters can have single or multiple peak wavelengths depending upon the application. By way of example, one of the red emitters can have a single peak radiation wavelength and the other red emitter can have multiple peak radiation wavelengths.

The process to select the desired radiation wavelength distributions for the radiation emitting devices to provide a sensor that can be used with a variety of oximeter processing and display units requires the identification of the spectral content set that corresponds to one or more of the correlation curves used by each oximeter processing and display unit. In one approach, the red and infrared emitters used in the conventional sensor manufactured specifically for an oximeter processing and display unit can be combined with the red and infrared emitters specifically manufactured for another manufacturer's oximeter processing and display unit. Thus, in this example the measuring means of the present invention would have two infrared emitters and two red emitters. As will be appreciated, the number of pairs of red and infrared emitters in the measuring means using this approach depends upon the number of oximeter processing and display units with which compatibility is desired. In another approach, two or more suitable red emitters and a common infrared emitter are selected such that the emitters produce a number of possible spectral content sets. The application of the oximeter processing and display unit's correlation curve to one of the resulting spectral content sets produces a blood oxygen saturation within an acceptable degree of accuracy of the actual oxygen saturation for the blood. The desired degree of accuracy is generally that specified by the particular manufacturer. Thus, the red and infrared emitters are selected such that the spectral content set when applied to the particular correlation curve for the oximeter processing and display unit produces a measurement for the blood oxygen saturation having a saturation error less than or equal to that specified by the manufacturer for the specific oximeter processing and display unit.

To permit each oximeter processing and display unit to determine the appropriate correlation curve to employ for the sensor assembly 10, the sensor assembly 10 includes identification means 50 and 54, each typically providing a different signal to the appropriate unit. By way of example, the identification means can be resistors with each resistor having a resistance that the corresponding oximeter processing and display unit would recognize as correlating to a specific correlation curve. The identification means are electrically energized one at a time (e.g., by being connected to different pins on the connector) such that, when the first identification means is biased by the first oximeter processing and display unit, the second identification means is not biased by the first oximeter processing and display unit, and, when the second identification means is biased by the second oximeter processing and display unit, the first identification means is not biased by the second oximeter processing and display unit. In this manner, the first oximeter processing and display unit sees only the first identification means, and the second oximeter processing and display unit sees only the second identification means.

As will be appreciated, the identification means can be not only resistors but also a host of other devices. By way of example, devices that vary an electrical parameter, namely current, voltage or resistance, in other manners can be employed. U.S. Pat. No. 4,700,708 to New, Jr., et al., which is incorporated herein by this reference, discloses that the identification means devices can include devices besides resistors, namely a connector wired to provide a digital value or binary array or a disposable memory containing the identification information.

Referring to FIGS. 2–5, the sensor housing includes a flexible leadframe 60 for selectively connecting the detector, radiation emitting devices, and identification means to the oximeter processing and display unit via the sensor and interconnect cables. The leadframe includes a plurality of leads 64a–h having a plurality of corresponding connection points 68a–h. Leads 64a,b and connection points 68a,b appropriately bias the detector 18. Leads 64c,d and connection points 68c,d appropriately bias the emitter 22. Leads 64e,f and connection points 68e,f appropriately bias the emitter 26 and 30. Leads 64c,g and 64h,g and connection points 68c,g and 68h,g appropriately connect the identification means 54 and 50, respectively.

Figure 6:
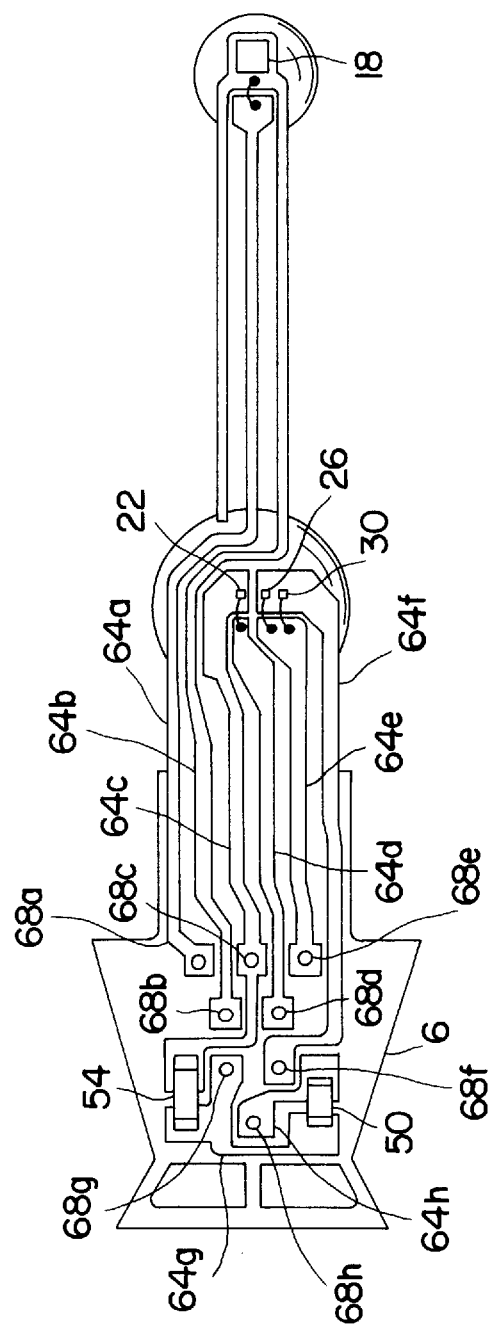
FIG. 6 is a view of a connector on the sensor leadframe assembly.
Figure 7A:
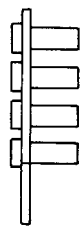
FIGS. 7A and 7B are side and front views of the connector attached to the leadframe assembly.
Figure 7B:
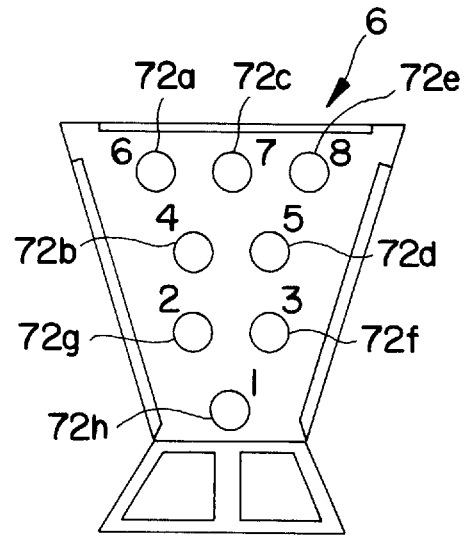
Figure 8:
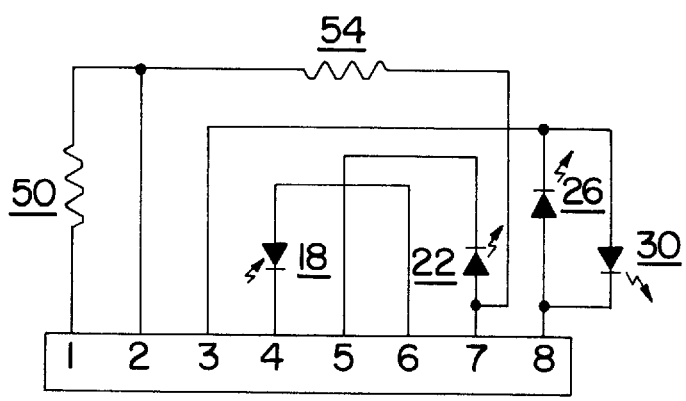
FIG. 8 is one embodiment of the sensor circuitry.

FIGS. 6, 7A and 7B illustrate the connection of the connector 6 to the emitters 22, 26 and 30 and the identification means 50 and 54. The emitters 26 and 30 are selectively activated by appropriately biasing the pins 72e,f which are connected to the connection points 68e,f. As shown in FIG. 8, the polarities of the emitters 26 and 30 are inverted with respect to one another such that only one can be activated at a time (i.e., they can be activated independently and selectively by alternating the bias applied to the connection points). The emitter 22 is activated by appropriately biasing the pins 72c,d which are connected to the connection points 68c,d. The detector 18 is activated by appropriately biasing the pins 72a,b which are connected to the connection points 68a,b. Finally, the identification means 50 and 54 are activated by biasing the pins 72h,g and 72c,g, respectively, which are connected to the connection points 68h,g and 68c,g, respectively.

Figure 2A:
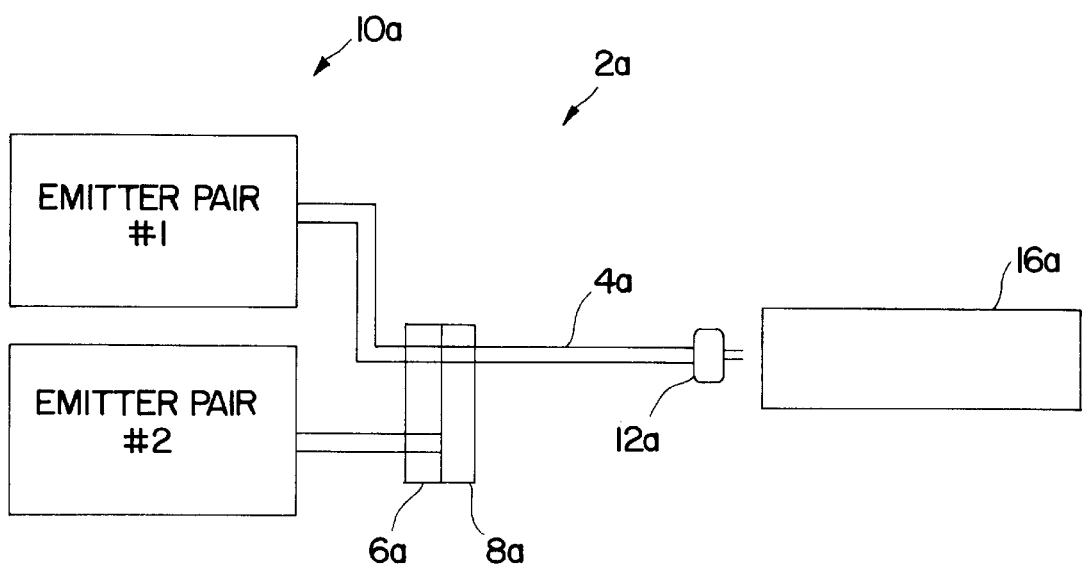
FIG. 2 depicts oximetry measuring means of the present invention being used with different oximeter processing and display units.
Figure 2B:
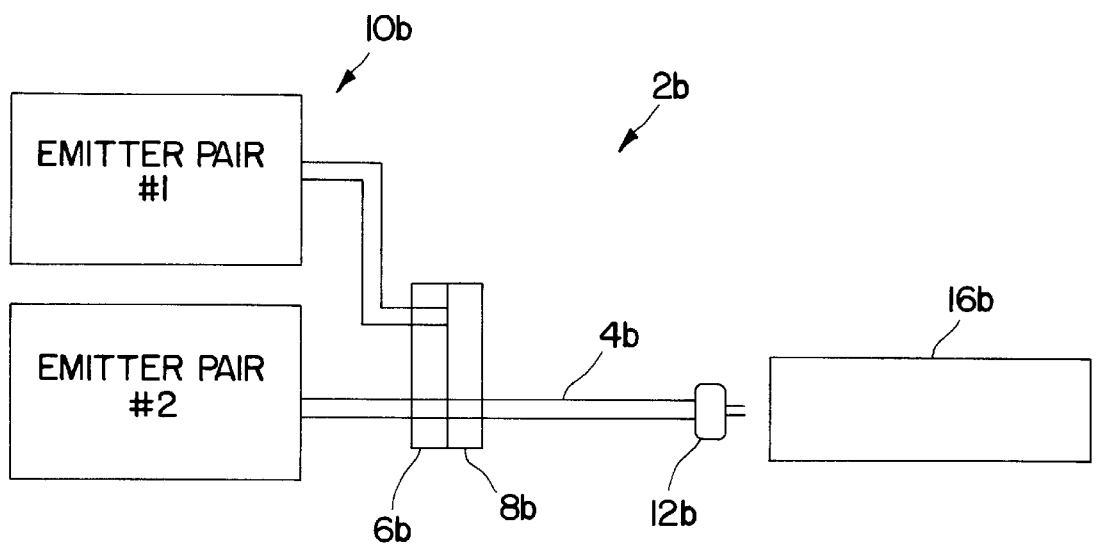
Figure 3:
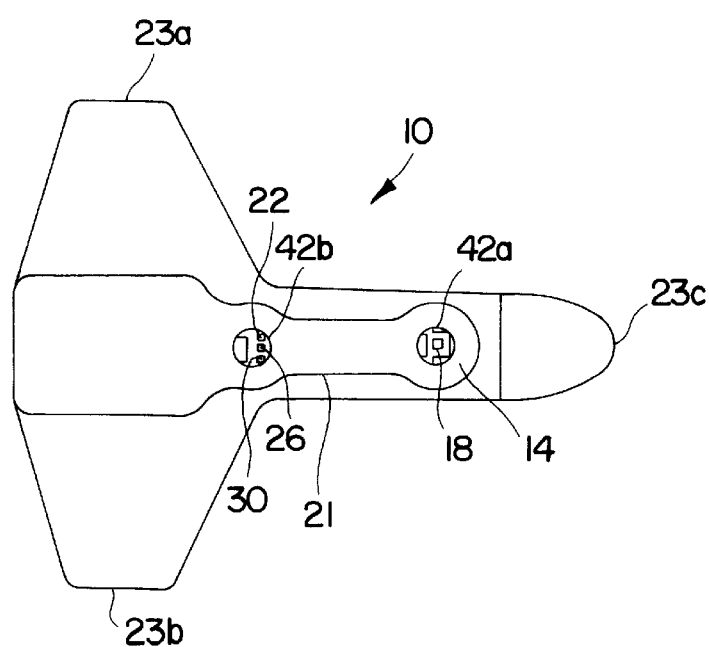
FIG. 3 is a plan view of the bottom of an oximetry measuring means according to an embodiment of the present invention.
Figure 4:
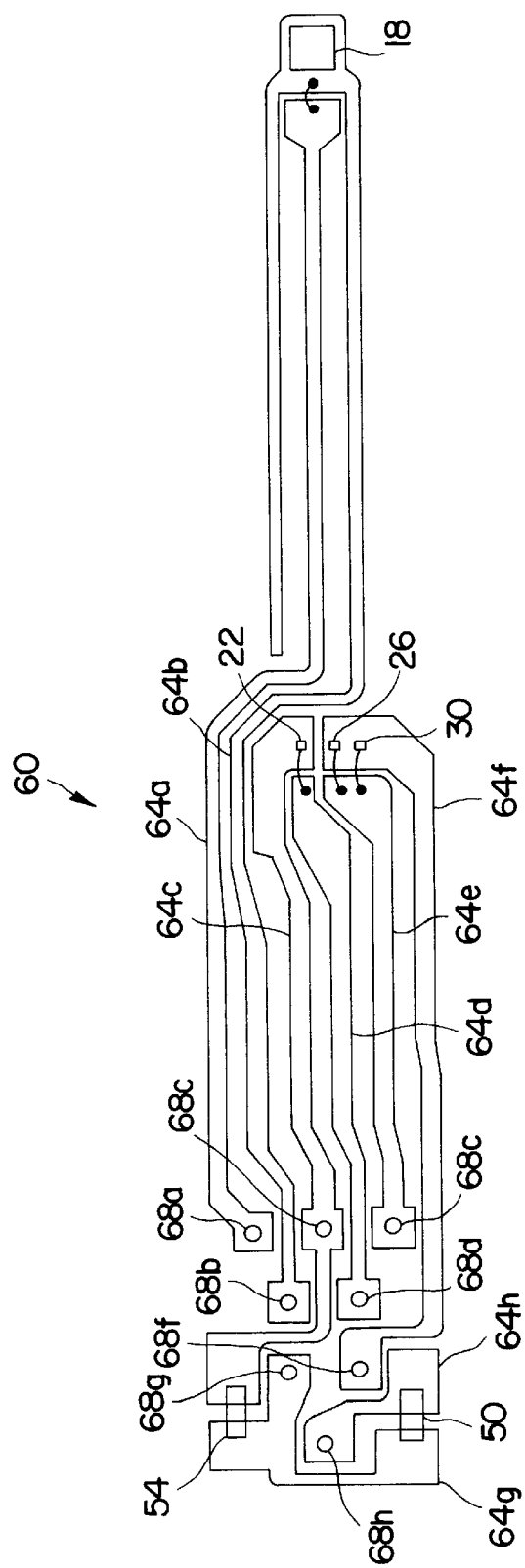
FIG. 4 is a plan view of a leadframe assembly in the oximetry measuring means.
Figure 5:
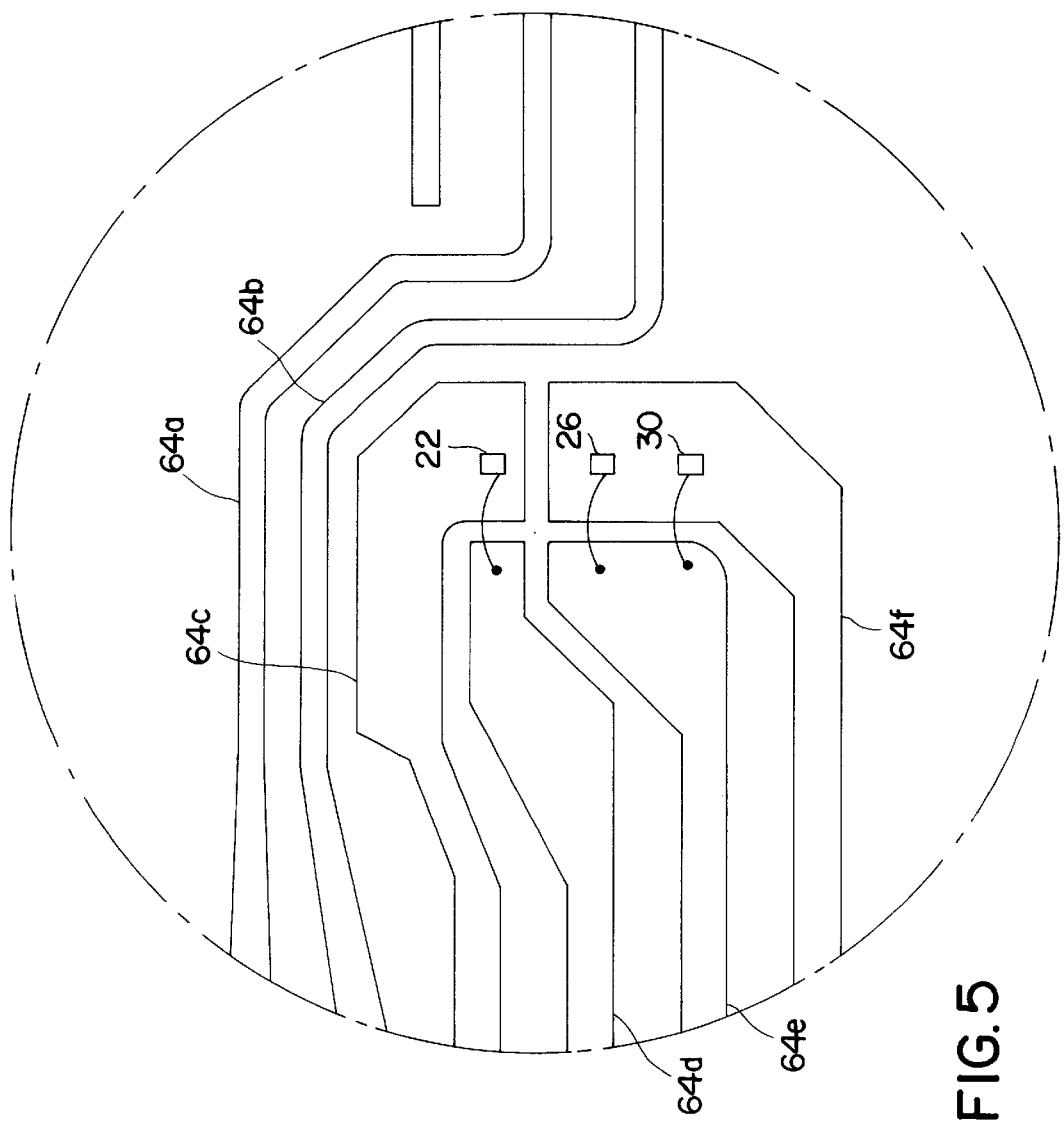
FIG. 5 is an expanded view of a portion of the leadframe assembly containing the LEDs.

Referring again to FIG. 2, the interconnect cable 4a,b provides for adaptability of the measuring means 10a,b with the first and second oximeter processing and display units 16a,b. The connectors 6a,b can be connected to either plug 8a or b. As shown in FIG. 2, however, the oximeter plugs 12a,b have the same or a different number of pins, differing pin configurations and/or housing shapes which are specific to the particular oximeter manufacturer. By way of example, the appropriate emitters are energized by the pin configuration of 8a and 8b. Each interconnection cable will thus incorporate the pin configuration on the other end of the interconnect cable to achieve compatibility between the sensor assembly 10 and the particular oximeter processing and display unit. Each interconnect cable can incorporate labeling which clearly indicates specifically which oximeter processing and display units the cable is compatible with. A color coding scheme, for example, is one method that can be used to indicate compatibility.

The operation of the sensor assembly 10 and attached oximeter processing and display unit will now be described with reference to FIG. 2. The connector 6 of the measuring means 10 is attached to the sensor plug 8 on the interconnect cable 4 and the oximeter plug 12 on the other end of interconnect cable is attached to the plug (not shown) on the oximeter processing and display unit 16.

The measuring means is positioned on the body part of the patient as described above. The oximeter appropriately energizes the pins of the oximeter plug 12 which then energizes the appropriate emitters via connector 8. The pin configuration depends upon the specific oximeter processing and display unit employed. In response to the applied voltage, the emitter 26 and either one of the emitters 22 or 30 are sequentially energized to provide separate spectral contents (i.e., the emitters 26 and either emitter 22 and/or 30 are activated at different times). The spectral components of each emitter sequentially pass through the tissue forming an absorbed portion and an unabsorbed portion of each spectral component. The unabsorbed portions of the spectral components are sequentially received by the detector 18 with separate measurements being taken for each portion. In response to the time-varying intensities of each of the unabsorbed radiation portions, the detector 18 produces a time-varying signal corresponding to each portion. Another measurement is taken with all of the emitters being "off" to quantify the noise from ambient radiation. Based on the identification means in the measuring means 10 biased by the particular oximeter processing and display unit, the oximeter processing and display unit selects an appropriate correlation curve and, based on the correlation curve, analyzes the time varying signals from the various measurements to estimate the oxygen saturation in the patient's bloodstream.

As will be appreciated, there are a variety of other embodiments of the present invention depending upon the application. In other embodiments, the sensor assembly can include more than one infrared and/or more than two red radiation emitting devices and, therefore, more than two resistors. One resistor is typically required for each of the possible combinations of infrared and red radiation emitting devices.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A sensor adaptable to first and second oximeter processing and display units, the sensor comprising:
   (a) measuring means for providing a signal that is a function of an unabsorbed portion of radiation passed by blood, said signal being employable to determine the oxygen saturation of blood, the measuring means comprising:
      (i) emitting means for irradiating said blood, comprising a plurality of emitters for providing radiation, each of the plurality of emitters providing a spectral content; and
      (ii) detecting means for detecting the unabsorbed portion of radiation passed by the blood; and
   (b) connecting means for connecting the measuring means with one of said first and second oximeter processing and display units such that, in a first mode when said measuring means is connected to said first oximeter processing and display unit, a first set of emitters is activated to produce a first set of spectral contents associated with the first set of emitters and, in a second mode when said measuring means is connected to said second oximeter processing and display unit, a second set of emitters is activated to produce a second set of spectral contents associated with the second set of emitters, wherein each of the first and second emitter sets includes at least two of the plurality of emitters and the first and second spectral content sets are different.

2. The sensor of claim 1, wherein the connecting means includes first and second interconnect cables respectively having first and second oximeter plugs, the first and second oximeter plugs having differing pin configurations such that said first interconnect cable connects to said first oximeter processing and display unit and said second interconnect cable connects to said second processing and display unit.

3. The sensor of claim 2, wherein the first and second interconnect cables respectively include first and second sensor plugs for connecting to a connector on the measuring means, wherein the connector is operable with both of said first and second sensor plugs.

4. The sensor of claim 3, wherein the first and second sensor plugs have the same geometrical pin configuration.

5. The sensor of claim 1, wherein the plurality of emitters includes first and second emitters, each of the first and second emitters being independently activated by an oximeter processing and display unit such that, when the first emitter is activated by the first oximeter processing and display unit, the second emitter is not activated by the first oximeter processing and display unit, and, when the second emitter is activated by the second oximeter processing and display unit, the first emitter is not activated by the second oximeter processing and display unit.

6. The sensor of claim 1, wherein the plurality of emitters includes a first emitter providing one of red and infrared radiation and second and third emitters each generating the other one of red and infrared radiation.

7. The sensor of claim 6, wherein the measuring means is separately activatable with a first pair of the first, second, and third emitters in the first set of emitters and with a second pair of the first, second and third emitters in the second set of emitters.

8. The sensor of claim 6, wherein the first emitter provides infrared radiation and each of the second and third emitters provides red radiation.

9. The sensor of claim 1, further comprising a first identification means for identifying a first correlation curve when the measuring means is connected to the first oximeter processing and display unit and a second identification means for identifying a second correlation curve when the measuring means is connected to the second oximeter processing and display unit.

10. The sensor of claim 1, further comprising:
   a first identification means for identifying a first correlation curve and a second identification means for identifying a second correlation curve; and wherein:
   said first and second emitter sets are different.

11. A sensor adaptable to a variety of oximeter processing and display units, the sensor comprising:
   (a) measuring means for providing a signal that is a function of an unabsorbed portion of radiation passed by blood, including:

(i) emitter means for said irradiating said blood, comprising a plurality of emitters respectively providing a plurality of spectral contents; and (ii) detecting means for receiving radiation passed by the blood; and (b) connecting means for connecting the measuring means with one of a first and second oximeter processing and display unit, wherein in a first mode when the connecting means is attached to the first oximeter processing and display unit a first set of the plurality of emitters is activated to generate a first spectral content set and in a second mode when the connecting means is attached to the second oximeter processing and display unit of a second set of the plurality of emitters are activated to generate a second spectral content set, with the first and second sets of emitters being different.

12. The sensor of claim 11, wherein the emitter means is operable so that each of the first and second spectral content sets include a different central wavelength.

13. The sensor of claim 11, further comprising a first identification means for identifying a first correlation curve and a second identification means for identifying a second correlation curve, the first and second correlation curves being different.

14. The sensor of claim 13, wherein the first and second spectral content sets differ from one another and wherein, in said first mode when said emitter means is connected to the first oximeter processing and display unit, said first spectral content set corresponds to the first correlation curve for said first oximeter processing and display unit and, in said second mode when said emitter means is connected to a second oximeter processing and display unit said second spectral content set corresponds to the second correlation curve for said second oximeter processing and display unit.

15. The sensor of claim 11, wherein such emitter means includes a plurality of emitters and, when operating in one of the first and second modes said measuring means being such that only one of the emitters is activatable at a time.

16. The sensor of claim 11, wherein the connecting means comprises:

a first interconnect cable having a first oximeter plug for connecting to a first oximeter processing and display unit; and a second interconnect cable having a second oximeter plug for connecting to a second oximeter processing and display unit, the first and second oximeter plugs having different pin configurations.

17. The sensor of claim 16, wherein the first interconnect cable has a first sensor plug and the second interconnect cable has a second sensor plug for connecting to a connector on said measuring means, wherein both the first and second sensor plugs are operable with said connector.

18. A sensor assembly adaptable to a variety of oximeter processing and display units, including a first oximeter processing and display unit having a corresponding first correlation curve and a second oximeter processing and display unit having a corresponding second correlation curve, the sensor assembly comprising:

(a) measuring means for providing a signal that is a function of an unabsorbed portion of radiation passed by blood including:

(i) emitter means for irradiating the blood;

(ii) first and second identification means, said first identification means for identifying the first correlation curve, said second identification means for identifying the second correlation curve; and (iii) detecting means for detecting said unabsorbed radiation; and (b) connecting means for connecting the measuring means to the first oximeter processing and display unit and the second oximeter processing and display unit, wherein when said connecting means is connected to one of the first oximeter processing and display unit and the second oximeter processing and display unit, the corresponding one of said first and second correlation curves is selected based on the corresponding one of said first and second identification means.

19. The sensor assembly of claim 18, wherein the first and second identification means provide a different signal from each other.

20. The sensor assembly of claim 18, wherein the emitter means comprises first, second and third emitters for providing radiation and said second and third emitters are separately activated such that, when the second emitter is activated, the third emitter emitting device is not activated, and, when the third emitter is activated, the second emitter is not activated.

21. The sensor assembly of claim 18, wherein:

the first and second identification means are connected to separate circuits such that, when the first identification means is biased by the first oximeter processing and display unit, the second identification means is not biased by of the first oximeter processing and display unit, and, when the second identification means is biased by the second oximeter processing and display unit, the first identification means is not biased by the second oximeter processing and display unit.

22. The sensor assembly of claim 18, wherein:

said emitter means comprises a plurality of emitters for providing radiation, a first set of the plurality of emitters produces a first spectral content set and a second set of the plurality of emitters produces a second spectral content set, wherein the first and second spectral content sets and first and second sets of emitters differ from one another and wherein, in a first mode when said emitter means is connected to said first oximeter processing and display unit, said first set of emitters is activated to produce the first spectral content set, corresponding to said first correlation curve and, in a second mode when said emitter means is connected to said second oximeter processing and display unit, said second set of emitters is activated to produce a second spectral content set corresponding to said second correlation curve.

23. A sensor assembly adaptable to a variety of oximeter and display units, including a first oximeter processing and display unit having a corresponding first correlation curve and to a second oximeter processing and display unit having a corresponding second correlation curve, the sensor comprising:

measuring means for providing a signal that is a function of an unabsorbed portion of radiation passed by blood including:

(i) a connector having a plurality of connecting elements, a first connecting element for connecting to the first oximeter processing and display unit and a second connecting element for connecting to the second oximeter processing and display unit;

(ii) first and second identification means connected to the connector, the first identification means for identifying the first correlation curve corresponding, the second identification means for identifying the second correlation curve;

(iii) first, second and third emitters, the first, second and third emitters being connected to the connector such that, when one of the first and second connector elements is connected to the corresponding one of the first and second oximeter processing and display units, only one pair of the first, second and third emitters is energized; and (iv) detecting means for detecting unabsorbed radiation, the detecting means being connected to the connector.

* * * * *